United States Patent
Yang

(10) Patent No.: US 10,392,624 B2
(45) Date of Patent: Aug. 27, 2019

(54) GENE ENGINEERING YEAST HAVING SACCHARIFICATION FUNCTION, METHOD OF PREPARING SAME, AND APPLICATION OF SAME

(71) Applicant: ANGEL YEAST CO., LTD., Yichang, Hubei (CN)

(72) Inventor: Sheng Yang, Yichang (CN)

(73) Assignee: ANGEL YEAST CO., LTD, Yichang (CN)

( * ) Notice: Subject to any disclaimer, the term of this patent is extended or adjusted under 35 U.S.C. 154(b) by 0 days.

(21) Appl. No.: 15/551,111

(22) PCT Filed: Feb. 4, 2016

(86) PCT No.: PCT/CN2016/073574
§ 371 (c)(1),
(2) Date: Aug. 15, 2017

(87) PCT Pub. No.: WO2016/127921
PCT Pub. Date: Aug. 18, 2016

(65) Prior Publication Data
US 2018/0030459 A1    Feb. 1, 2018

(30) Foreign Application Priority Data

Feb. 15, 2015  (CN) .......................... 2015 1 0083082

(51) Int. Cl.
| | | |
|---|---|---|
| *C12P 7/06* | (2006.01) | |
| *C12N 1/14* | (2006.01) | |
| *C12N 15/81* | (2006.01) | |
| *C12N 9/34* | (2006.01) | |
| *C12P 7/10* | (2006.01) | |
| *C12R 1/865* | (2006.01) | |

(52) U.S. Cl.
CPC ........... *C12N 15/81* (2013.01); *C12N 9/2428* (2013.01); *C12P 7/06* (2013.01); *C12P 7/10* (2013.01); *C12Y 302/01003* (2013.01); *C12R 1/865* (2013.01); *Y02E 50/16* (2013.01); *Y02E 50/17* (2013.01)

(58) Field of Classification Search
CPC ....... C12P 7/06; C12P 7/16; C12Y 302/01001
USPC ................................................ 435/161, 254.2
See application file for complete search history.

(56) References Cited

U.S. PATENT DOCUMENTS

2008/0213195 A1   9/2008  Szeles et al.
2013/0323822 A1  12/2013  Brevnova et al.

FOREIGN PATENT DOCUMENTS

| CN | 103695389 A | 4/2014 | |
|---|---|---|---|
| WO | WO2014151318 A2 * | 3/2014 | ............... C12Q 1/68 |

OTHER PUBLICATIONS

Written Opinion PCT/CN2016/073574 (2016).*
Genbank Accession No. AJ311587.1. Apr. 15, 2005. Hostinova et al.
Genbank Accession No. CAC83969. Apr. 15, 2005. Hostinova et al.
Horvathova et al., Evaluation of the glucoamylase Glm from Saccharomycopsis fibuligera IFO 0111 in hydrolyzing the corn starch. Biologia. 2004;59(3):361-365.
Ma et al., Advances on Structure and Function of Glucoamylase. Letters Biotechnology. Nov. 2005;16(6):677-680.

* cited by examiner

*Primary Examiner* — Tekchand Saidha
(74) *Attorney, Agent, or Firm* — Wolf, Greenfield & Sacks, P.C.

(57) ABSTRACT

A gene engineering yeast having a saccharification function, a method of preparing same, and an application of same, a nucleotide sequence for encoding glucose amylase, where: (a) the nucleotide sequence is an amino acid sequence shown by the code SEQ ID NO:16; or (b) the sequence of the encoding region of the glucose amylase of the nucleotide sequence and the nucleotide sequence shown by SEQ ID NO:15 have a similarity ≥80%.

5 Claims, 1 Drawing Sheet
Specification includes a Sequence Listing.

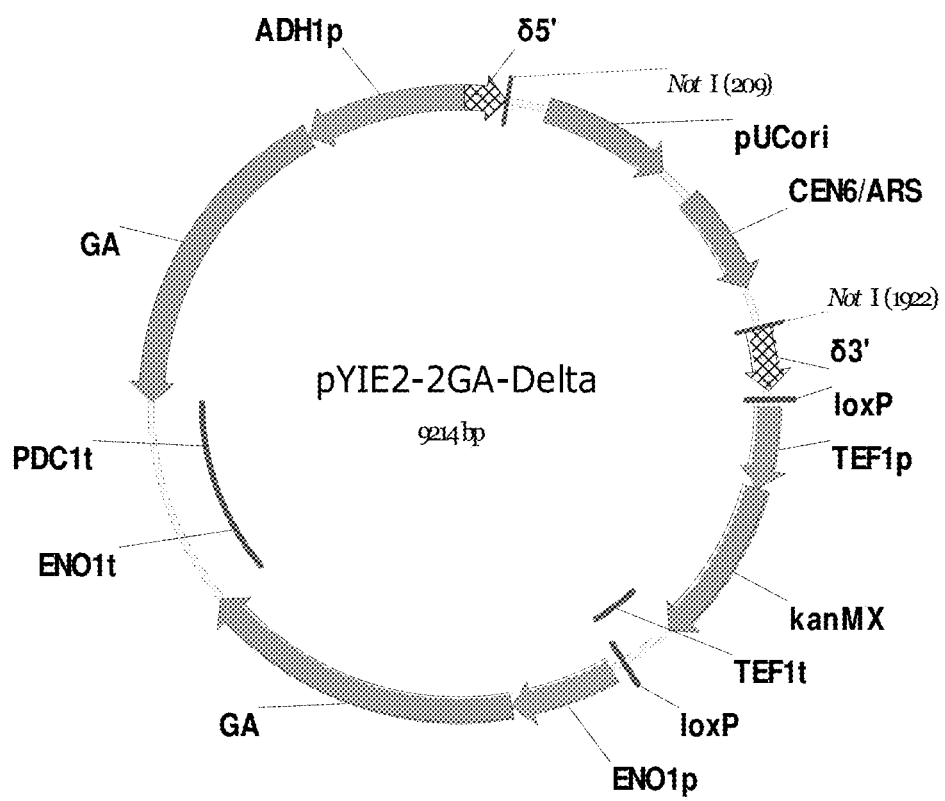

SEQUENCE LISTING

```
<160> NUMBER OF SEQ ID NOS: 36

<210> SEQ ID NO 1
<211> LENGTH: 31
<212> TYPE: DNA
<213> ORGANISM: Artificial sequence
<220> FEATURE:
<223> OTHER INFORMATION: primer

<400> SEQUENCE: 1
taggatcctg ttggaataga aatcaactat c                              31

<210> SEQ ID NO 2
<211> LENGTH: 33
<212> TYPE: DNA
<213> ORGANISM: Artificial sequence
```

```
<220> FEATURE:
<223> OTHER INFORMATION: primer

<400> SEQUENCE: 2
gtaggtaccg gccactagtg gatctgatat cac                                33

<210> SEQ ID NO 3
<211> LENGTH: 34
<212> TYPE: DNA
<213> ORGANISM: Artificial sequence
<220> FEATURE:
<223> OTHER INFORMATION: primer

<400> SEQUENCE: 3
gtaggtaccc ttctaggcgg gttatctact gatc                               34

<210> SEQ ID NO 4
<211> LENGTH: 45
<212> TYPE: DNA
<213> ORGANISM: Artificial sequence
<220> FEATURE:
<223> OTHER INFORMATION: primer

<400> SEQUENCE: 4
aaaacggtca atctgatcat tttgatttag tgtttgtgtg ttgat                   45

<210> SEQ ID NO 5
<211> LENGTH: 45
<212> TYPE: DNA
<213> ORGANISM: Artificial sequence
<220> FEATURE:
<223> OTHER INFORMATION: primer

<400> SEQUENCE: 5
cacacaaaca ctaaatcaaa atgatcagat tgaccgtttt cttga                   45

<210> SEQ ID NO 6
<211> LENGTH: 45
<212> TYPE: DNA
<213> ORGANISM: Artificial sequence
<220> FEATURE:
<223> OTHER INFORMATION: primer

<400> SEQUENCE: 6
agaaggctta atcaaaagct ttacaataat tcgatcaact tgttt                   45

<210> SEQ ID NO 7
<211> LENGTH: 45
<212> TYPE: DNA
<213> ORGANISM: Artificial sequence
<220> FEATURE:
<223> OTHER INFORMATION: primer

<400> SEQUENCE: 7
agttgatcga attattgtaa agcttttgat taagccttct agtcc                   45

<210> SEQ ID NO 8
<211> LENGTH: 45
<212> TYPE: DNA
<213> ORGANISM: Artificial sequence
<220> FEATURE:
<223> OTHER INFORMATION: primer

<400> SEQUENCE: 8
taggatccta catcatatgg aaagaggttt agacattggc tcttc                   45
```

```
<210> SEQ ID NO 9
<211> LENGTH: 33
<212> TYPE: DNA
<213> ORGANISM: Artificial sequence
<220> FEATURE:
<223> OTHER INFORMATION: primer

<400> SEQUENCE: 9
taggatcccg attttttct aaaccgtgga ata                              33

<210> SEQ ID NO 10
<211> LENGTH: 45
<212> TYPE: DNA
<213> ORGANISM: Artificial sequence
<220> FEATURE:
<223> OTHER INFORMATION: primer

<400> SEQUENCE: 10
aaaacggtca atctgatcat tgtatatgag atagttgatt gtatg                45

<210> SEQ ID NO 11
<211> LENGTH: 45
<212> TYPE: DNA
<213> ORGANISM: Artificial sequence
<220> FEATURE:
<223> OTHER INFORMATION: primer

<400> SEQUENCE: 11
aatcaactat ctcatataca atgatcagat tgaccgtttt cttga                45

<210> SEQ ID NO 12
<211> LENGTH: 45
<212> TYPE: DNA
<213> ORGANISM: Artificial sequence
<220> FEATURE:
<223> OTHER INFORMATION: primer

<400> SEQUENCE: 12
ataattagag attaaatcgc ttacaataat tcgatcaact tgttt                45

<210> SEQ ID NO 13
<211> LENGTH: 45
<212> TYPE: DNA
<213> ORGANISM: Artificial sequence
<220> FEATURE:
<223> OTHER INFORMATION: primer

<400> SEQUENCE: 13
agttgatcga attattgtaa gcgatttaat ctctaattat tagtt                45

<210> SEQ ID NO 14
<211> LENGTH: 36
<212> TYPE: DNA
<213> ORGANISM: Artificial sequence
<220> FEATURE:
<223> OTHER INFORMATION: primer

<400> SEQUENCE: 14
catcatatgt ttcaatcatt ggagcaatca ttttac                          36

<210> SEQ ID NO 15
<211> LENGTH: 1548
<212> TYPE: DNA
<213> ORGANISM: homo sapiens

<400> SEQUENCE: 15
```

-continued

```
atgatcagat tgaccgtttt cttgaccgct gttttgctg ctgttgcttc ttgtgttcca      60
gttgaattgg ataagagaaa caccggtcat ttccaagctt attctggtta taccgttgct    120
agatctaact tcacccaatg gattcatgaa caaccagctg tttcttggta ctacttgttg    180
caaaacatcg attacccaga aggtcaattc aaatctgcta accaggtgt tgttgttgct    240
tctccatcta catctgaacc agattacttc taccaatgga ctagagatac cgctattacc    300
ttcttgtcct tgattgctga agttgaagat cattctttct ccaacactac cttggctaag    360
gttgtcgaat attcatttc caacacctac accttgcaaa gagtttctaa tccatccggt     420
aacttcgatt ctccaaatca tgatggttg ggtgaaccta agttcaacgt tgatgatact     480
gcttatacag cttcttgggg tagaccacaa atgatggtc cagctttgag agcttacgct     540
atttctagat acttgaacgc tgttgctaag cacaacaacg taaattatt attggccggt     600
caaaacggta ttccttattc ttctgcttcc gatatctact ggaagattat taagccagac    660
ttgcaacatg tttctactca ttggtctacc tctggttttg atttgtggga agaaaatcaa    720
ggtactcatt tcttcaccgc tttggttcaa ttgaaggctt tgtcttacgg tattccattg    780
tctaagacct acaatgatcc aggtttcact tcttggttgg aaaaacaaaa ggatgccttg    840
aactcctaca ttaactcttc cggtttcgtt aactctggta aaaagcacat cgttgaatct    900
ccacaattgt catctagagg tggttttggat tctgctactt atattgctgc cttgatcacc   960
catgatatcg gtgatgatga tacttacacc ccattcaatg ttgataactc ctacgttttg   1020
aactccttgt attacctatt ggtcgacaac aagaacagat acaagatcaa cggtaactac   1080
aaagctggtg ctgctgttgg tagatatcct gaagatgttt acaacggtgt tggtacttct   1140
gaaggtaatc catggcaatt ggctactgct tatgctggtc aaactttta caccttggcc   1200
tacaattcct tgaagaacaa gaagaacttg gtcatcgaaa agttgaacta cgacttgtac   1260
aactccttca ttgctgattt gtccaagatt gattcttcct acgcttcaa ggattctttg    1320
actttgacct acggttccga taactacaag aacgttatca gtccttgtt gcaattcggt    1380
gactcattct tgaaggtttt gttggatcac atcgatgaca acggtcaatt gactgaagaa    1440
atcaacagat acaccggttt tcaagctggt gcagtttctt tgacttggtc atctggttct    1500
ttgttgtctg ctaatagagc cagaaacaag ttgatcgaat tattgtaa                 1548
```

<210> SEQ ID NO 16
<211> LENGTH: 515
<212> TYPE: PRT
<213> ORGANISM: homo sapiens

<400> SEQUENCE: 16

```
Met Ile Arg Leu Thr Val Phe Leu Thr Ala Val Phe Ala Ala Val Ala
1               5                   10                  15

Ser Cys Val Pro Val Glu Leu Asp Lys Arg Asn Thr Gly His Phe Gln
                20                  25                  30

Ala Tyr Ser Gly Tyr Thr Val Ala Arg Ser Asn Phe Thr Gln Trp Ile
            35                  40                  45

His Glu Gln Pro Ala Val Ser Trp Tyr Leu Leu Gln Asn Ile Asp
        50                  55                  60

Tyr Pro Glu Gly Gln Phe Lys Ser Ala Lys Pro Gly Val Val Val Ala
65                  70                  75                  80

Ser Pro Ser Thr Ser Glu Pro Asp Tyr Phe Tyr Gln Trp Thr Arg Asp
                85                  90                  95
```

-continued

```
Thr Ala Ile Thr Phe Leu Ser Leu Ile Ala Glu Val Glu Asp His Ser
            100                 105                 110
Phe Ser Asn Thr Thr Leu Ala Lys Val Val Glu Tyr Tyr Ile Ser Asn
        115                 120                 125
Thr Tyr Thr Leu Gln Arg Val Ser Asn Pro Ser Gly Asn Phe Asp Ser
    130                 135                 140
Pro Asn His Asp Gly Leu Gly Glu Pro Lys Phe Asn Val Asp Asp Thr
145                 150                 155                 160
Ala Tyr Thr Ala Ser Trp Gly Arg Pro Gln Asn Asp Gly Pro Ala Leu
                165                 170                 175
Arg Ala Tyr Ala Ile Ser Arg Tyr Leu Asn Ala Val Ala Lys His Asn
            180                 185                 190
Asn Gly Lys Leu Leu Leu Ala Gly Gln Asn Gly Ile Pro Tyr Ser Ser
        195                 200                 205
Ala Ser Asp Ile Tyr Trp Lys Ile Ile Lys Pro Asp Leu Gln His Val
    210                 215                 220
Ser Thr His Trp Ser Thr Ser Gly Phe Asp Leu Trp Glu Glu Asn Gln
225                 230                 235                 240
Gly Thr His Phe Phe Thr Ala Leu Val Gln Leu Lys Ala Leu Ser Tyr
                245                 250                 255
Gly Ile Pro Leu Ser Lys Thr Tyr Asn Asp Pro Gly Phe Thr Ser Trp
            260                 265                 270
Leu Glu Lys Gln Lys Asp Ala Leu Asn Ser Tyr Ile Asn Ser Ser Gly
        275                 280                 285
Phe Val Asn Ser Gly Lys Lys His Ile Val Glu Ser Pro Gln Leu Ser
    290                 295                 300
Ser Arg Gly Gly Leu Asp Ser Ala Thr Tyr Ile Ala Ala Leu Ile Thr
305                 310                 315                 320
His Asp Ile Gly Asp Asp Thr Tyr Thr Pro Phe Asn Val Asp Asn
                325                 330                 335
Ser Tyr Val Leu Asn Ser Leu Tyr Leu Leu Val Asp Asn Lys Asn
            340                 345                 350
Arg Tyr Lys Ile Asn Gly Asn Tyr Lys Ala Gly Ala Ala Val Gly Arg
        355                 360                 365
Tyr Pro Glu Asp Val Tyr Asn Gly Val Gly Thr Ser Glu Gly Asn Pro
    370                 375                 380
Trp Gln Leu Ala Thr Ala Tyr Ala Gly Gln Thr Phe Tyr Thr Leu Ala
385                 390                 395                 400
Tyr Asn Ser Leu Lys Asn Lys Asn Leu Val Ile Glu Lys Leu Asn
                405                 410                 415
Tyr Asp Leu Tyr Asn Ser Phe Ile Ala Asp Leu Ser Lys Ile Asp Ser
            420                 425                 430
Ser Tyr Ala Ser Lys Asp Ser Leu Thr Leu Thr Tyr Gly Ser Asp Asn
        435                 440                 445
Tyr Lys Asn Val Ile Lys Ser Leu Leu Gln Phe Gly Asp Ser Phe Leu
    450                 455                 460
Lys Val Leu Leu Asp His Ile Asp Asp Asn Gly Gln Leu Thr Glu Glu
465                 470                 475                 480
Ile Asn Arg Tyr Thr Gly Phe Gln Ala Gly Ala Val Ser Leu Thr Trp
                485                 490                 495
Ser Ser Gly Ser Leu Leu Ser Ala Asn Arg Ala Arg Asn Lys Leu Ile
            500                 505                 510
Glu Leu Leu
```

<210> SEQ ID NO 17
<211> LENGTH: 58
<212> TYPE: DNA
<213> ORGANISM: Artificial sequence
<220> FEATURE:
<223> OTHER INFORMATION: primer

<400> SEQUENCE: 17
ttcaaatctt gtttgtttgc ccataccagc agtactgttg aatagaaat caactatc    58

<210> SEQ ID NO 18
<211> LENGTH: 40
<212> TYPE: DNA
<213> ORGANISM: Artificial sequence
<220> FEATURE:
<223> OTHER INFORMATION: primer

<400> SEQUENCE: 18
aaaccgcctc tgcggccgcc taatattacg attattcctc    40

<210> SEQ ID NO 19
<211> LENGTH: 40
<212> TYPE: DNA
<213> ORGANISM: Artificial sequence
<220> FEATURE:
<223> OTHER INFORMATION: primer

<400> SEQUENCE: 19
aatattaggc ggccgcagag gcggtttgcg tattgggcgc    40

<210> SEQ ID NO 20
<211> LENGTH: 45
<212> TYPE: DNA
<213> ORGANISM: Artificial sequence
<220> FEATURE:
<223> OTHER INFORMATION: primer

<400> SEQUENCE: 20
aaatatgtat ccgctcatga gatctaggtg aagatccttt ttgat    45

<210> SEQ ID NO 21
<211> LENGTH: 45
<212> TYPE: DNA
<213> ORGANISM: Artificial sequence
<220> FEATURE:
<223> OTHER INFORMATION: primer

<400> SEQUENCE: 21
aaaggatctt cacctagatc tcatgagcgg atacatattt gaatg    45

<210> SEQ ID NO 22
<211> LENGTH: 40
<212> TYPE: DNA
<213> ORGANISM: Artificial sequence
<220> FEATURE:
<223> OTHER INFORMATION: primer

<400> SEQUENCE: 22
tctacatagc ggccgcagcc ccgacacccg ccaacacccg    40

<210> SEQ ID NO 23
<211> LENGTH: 40
<212> TYPE: DNA
<213> ORGANISM: Artificial sequence -continued
<220> FEATURE:
<223> OTHER INFORMATION: primer

<400> SEQUENCE: 23
gtgtcggggc tgcggccgct atgtagaaat atagattcca        40

<210> SEQ ID NO 24
<211> LENGTH: 59
<212> TYPE: DNA
<213> ORGANISM: Artificial sequence
<220> FEATURE:
<223> OTHER INFORMATION: primer

<400> SEQUENCE: 24
gttgtcgacc tgcagcgtac gaagcttcag ctggcatggg ggttctctgg aacagctga        59

<210> SEQ ID NO 25
<211> LENGTH: 60
<212> TYPE: DNA
<213> ORGANISM: Artificial sequence
<220> FEATURE:
<223> OTHER INFORMATION: primer

<400> SEQUENCE: 25
cacctgcttc atcagctgtt ccagagaacc cccatgccag ctgaagcttc gtacgctgca        60

<210> SEQ ID NO 26
<211> LENGTH: 60
<212> TYPE: DNA
<213> ORGANISM: Artificial sequence
<220> FEATURE:
<223> OTHER INFORMATION: primer

<400> SEQUENCE: 26
ctcatcgtga tgtagtcaac cctcttcttg ttttaggcca ctagtggatc tgatatcacc        60

<210> SEQ ID NO 27
<211> LENGTH: 60
<212> TYPE: DNA
<213> ORGANISM: Artificial sequence
<220> FEATURE:
<223> OTHER INFORMATION: primer

<400> SEQUENCE: 27
gaagttatta ggtgatatca gatccactag tggcctaaaa caagaagagg gttgactaca        60

<210> SEQ ID NO 28
<211> LENGTH: 80
<212> TYPE: DNA
<213> ORGANISM: Artificial sequence
<220> FEATURE:
<223> OTHER INFORMATION: primer

<400> SEQUENCE: 28
tcaaaaaaat ggcattattc taagtaagtt aaatatccgt aatctttaaa cactaaaagc        60
gctaatttga tttgtctctc        80

<210> SEQ ID NO 29
<211> LENGTH: 80
<212> TYPE: DNA
<213> ORGANISM: Artificial sequence
<220> FEATURE:
<223> OTHER INFORMATION: primer

<400> SEQUENCE: 29

```
tatgaaaggg tgagcgacca gcaacgagag agacaaatca aattagcgct tttagtgttt    60
aaagattacg gatatttaac                                                80

<210> SEQ ID NO 30
<211> LENGTH: 80
<212> TYPE: DNA
<213> ORGANISM: Artificial sequence
<220> FEATURE:
<223> OTHER INFORMATION: primer

<400> SEQUENCE: 30
ctcacgagta attcttgcaa atgcctatta tgcagatgtt ataatatctg tgcgtttgat    60
tcaggtcaaa atggattcag                                                80

<210> SEQ ID NO 31
<211> LENGTH: 80
<212> TYPE: DNA
<213> ORGANISM: Artificial sequence
<220> FEATURE:
<223> OTHER INFORMATION: primer

<400> SEQUENCE: 31
cacaatgatg ttttcgatgc tgtaaacgtc cctgaatcca ttttgacctg aatcaaacgc    60
acagatatta taacatctgc                                                80

<210> SEQ ID NO 32
<211> LENGTH: 80
<212> TYPE: DNA
<213> ORGANISM: Artificial sequence
<220> FEATURE:
<223> OTHER INFORMATION: primer

<400> SEQUENCE: 32
atttacagaa gttggaaggc tggtattgtt gttcaagcca gcggtgccag ttggaaggac    60
actttccaaa aagagagcta                                                80

<210> SEQ ID NO 33
<211> LENGTH: 80
<212> TYPE: DNA
<213> ORGANISM: Artificial sequence
<220> FEATURE:
<223> OTHER INFORMATION: primer

<400> SEQUENCE: 33
tagcatattt taagtttctc tcgattttct tagctctctt tttggaaagt gtccttccaa    60
ctggcaccgc tggcttgaac                                                80

<210> SEQ ID NO 34
<211> LENGTH: 80
<212> TYPE: DNA
<213> ORGANISM: Artificial sequence
<220> FEATURE:
<223> OTHER INFORMATION: primer

<400> SEQUENCE: 34
gcttgtttat cttgcacatc acatcagcgg aacatatgct cacccagtcg catgacttga    60
atggtgtgat tctctcgaag                                                80

<210> SEQ ID NO 35
<211> LENGTH: 80
<212> TYPE: DNA
<213> ORGANISM: Artificial sequence
```

```
<220> FEATURE:
<223> OTHER INFORMATION: primer

<400> SEQUENCE: 35
agcacatggc cgagcttgaa tgttaaaccc ttcgagagaa tcacaccatt caagtcatgc    60
gactgggtga gcatatgttc                                               80

<210> SEQ ID NO 36
<211> LENGTH: 60
<212> TYPE: DNA
<213> ORGANISM: Artificial sequence
<220> FEATURE:
<223> OTHER INFORMATION: primer

<400> SEQUENCE: 36
tagttagtag atgatagttg atttctattc caacagtact gctggtatgg gcaaacaaac    60
```

GENE ENGINEERING YEAST HAVING SACCHARIFICATION FUNCTION, METHOD OF PREPARING SAME, AND APPLICATION OF SAME

RELATED APPLICATIONS

This application is a national stage filing under 35 U.S.C. § 371 of International Application PCT/CN2016/073574 entitled "GENE ENGINEERING YEAST HAVING SACCHARIFICATION FUNCTION, METHOD OF PREPARING SAME, AND APPLICATION OF SAME" filed Feb. 4, 2016, which claims priority to CN Application No. 201510083082.5, filed Feb. 15, 2015, the entire disclosure of each of which is incorporated by reference herein in its entirety.

TECHNICAL FIELD

The present invention relates to gene engineering yeast having saccharification function, method of preparation same, and application of same.

BACKGROUND

Ethanol is an important raw material for food and chemical industry and a renewable fuel. At present, cellulose ethanol production technology is under development, and can not meet the requirements of commercialization. The ethanol on sale is mainly produced from corn and sugar cane as the raw materials, and such raw materials are rich in starch and sugar, respectively. In China, in addition to corn, wheat and cassava and other starch-rich raw materials are also used to produce ethanol. It is very important to improve the existing technology and reduce the processing cost of starch raw materials to ethanol.

At present, the ethanol production from starch raw materials needs a number of steps, such as: crushing, liquefaction, saccharification, fermentation, distillation and so on. In these steps, the addition of saccharifying enzymes (ie, glucose amylase, EC 3.2.1.3) is required in the saccharification process for degrading the starch into glucose. The enzyme can be purchased directly from the market. The cost of the saccharification enzymes needed for the production of one ton of ethanol is about 100 rmb. If the fermentative strains possess the function of a glucoamylase, then the amount of glucoamylase can be reduced. Therefore, for reducing the production cost of ethanol, it is necessary to develop *Saccharomyces cerevisiae* with saccharification function.

From the mid-1980s, glucoamylases from various sources were cloned into *Saccharomyces cerevisiae* to construct yeast strains with saccharification function.

In 1985, Cetus published a paper on Science and reported that glucamylase from *Aspergillus awamori* was cloned into *Saccharomyces cerevisiae* by genetic engineering. The recombinant strain was able to grow on starch as the sole carbon source. In addition to *Aspergillus awamori* sources, *Rhizopus oryzae* and *Aspergillus niger*-derived glucamylases are often used. For increasing the ability to saccharify starch, α-amylase (EC3.2.1.1) was subsequently cloned into *Saccharomyces cerevisiae*, for saccharifying starch in combination with glucoamylase. *Bacillus amyloliquefaciens, Bacillus stearothermophilus, Bacillus licheniformis, Bacillus subtilis, Streptococcus bovis, Debaryomyces occidentalis* and barley (*Hordeum vulgare*) etc. are common sources of α-amylase. It has been reported that the co-expression of α-amylase derived from *streptococcus bovis*, not from *bacillus stearothermophilus* with *Rhizopus oryzae*-derived glucoamylase can induce the saccharification and fermentation of the recombinant strain with a raw starch as a raw material. The reason is that the *bacillus stearothermophilus*-derived α-amylase does not have a starch-binding domain, and its co-expression with *Rhizopus oryzae*-derived glucoamylase can only cause the saccharification and fermentation of the recombinant strain with a soluble starch as a raw material. In addition, debranching enzymes (E.C.3.2.1.33 pullulanase and isoamylase) and maltose transporters were also cloned into *Saccharomyces cerevisiae* to enhance the saccharification and fermentation of the starch.

Recently, some research teams use surface display technology to construct *Saccharomyces diastaticus*, while others are committed to construct *Saccharomyces diastaticus* using the secretory expression technology. However, the current research is mostly based on basic research, and it is difficult to meet the requirements of industrial applications. For example, the used host is a laboratory strain with auxotrophic phenotype, which makes the recombinant bacteria not strong enough, and brings about some other issues, such as low growth rate and low fermentation performance; and a 2 μm of plasmid expression vector is usually used, the benefit of which is that it is a multi-copy; and the disadvantage of which is that, under the conditions of the non-selective pressure, it is easy to lose.

Therefore, it is still necessary to develop a *Saccharomyces cerevisiae* with efficient saccharification function qualified with the requirements of industrial application.

SUMMARY OF THE INVENTION

The object of the present invention is to provide *Saccharomyces cerevisiae* with efficient saccharification function.

In the first aspect of the present invention, a nucleotide sequence encoding glucamylase is provided, and the nucleotide sequence is selected from a group consisting of:

(a) the amino acid sequence shown in SEQ ID NO: 16 is encoded by the nucleotide sequence;

(b) the sequence of the glucoamylase-coding region of the nucleotide sequence has ≥80% identity with the nucleotide sequence shown in SEQ ID NO:15.

In another preferred embodiment, the nucleotide sequence is shown in SEQ ID NO: 15.

In the second aspect of the present invention, an expression vector is provided, comprising the nucleotide sequence according to the first aspect of the present invention.

In the third aspect of the present invention, a yeast host cell is provided, wherein the yeast host cell comprises the expression vector according to the second aspect of the present invention or has the sequence of the glucoamylase-coding region of the nucleotide sequence according to the first aspect of the present invention integrated into the genome thereof.

In another preferred embodiment, an antibiotics resistance gene is not included in the yeast host cell.

In another preferred embodiment, the yeast host cell is *Saccharomyces cerevisiae*, with Accession No. CCTCC M 2014657.

In the fourth aspect of the present invention, a method for producing glucoamylase is provided, comprising steps of:

(a) under a suitable expression condition, culturing the yeast host cell according to the third aspect of the present invention, thereby expressing the glucose amylase;

(b) isolating and purifying the glucoamylase expressed in step (a).

In the fifth aspect of the present invention, a method for producing a yeast host cell is provded, comprising steps of:

(a) preparing three fragments, which is ENO1p-GA-ENO1t, delta5'-pUCori-CEN6/ARS-delta3'-loxP-TEF1p-KanMX-TEF1t-loxP, ADH1p-GA-PDC1t, respectively;

(b) connecting the three fragments obtained in step a) to obtain a target plasmid, pYIE2-2GA-delta;

(c) linearizing pYIE2-2GA-delta obtained in step b) by NotI, and transforming *Saccharomyces cerevisiae* to obtain a transformant;

(d) eliminating the resistance gene in a strain cultured from the transformant obtained in step c) to obtain the recombinant yeast.

In the sixth aspect of the present invention, a use of yeast host cell according to the third aspect of the present invention is provided for producing ethanol through fermentation.

In the seventh aspect of the present invention, a method for producing ethanol is provided, using the yeast host cell according to the third aspect of the present invention for producing ethanol through fermentation.

In the invention, *Saccharomyces cerevisiae* CCTCC M94055 is used as a host cell, and the multi-copy integration technique is adopted to integrate the saccharifying enzyme, i.e., the glucoamylase into the genome, and then the antibiotic resistance gene is eliminated and the obtained recombinant *Saccharomyces cerevis* possesses efficient saccharification function.

It is to be understood that within the scope of the present invention, each foregoing technical feature of the present invention and each technical feature described in detail below (e.g., examples) may be combined with each other to form a new or preferred technical solution, which is not elaborated herein for the sake of brevity.

DESCRIPTION OF DRAWINGS

FIG. 1 shows a pattern of pYIE2-2GA-delta plasmid.

DETAILED DESCRIPTION OF THE INVENTION

Through a long-term and in-depth study, the inventors of the present application use *Saccharomyces cerevisiae* CCTCC M94055 as a host cell, adpot the multi-copy integration technique to integrate the saccharifying enzyme, i.e., the glucoamylase into the genome, and then eliminate the antibiotic resistance gene. The inventors have unexpectedly discovered that the *Saccharomyces cerevis* with efficient saccharification function can be obtained, and ethanol can be produced in high yield without additional saccharifying enzyme for ethanol fermentation. Based on the above findings, the present invention was completed.

A *Saccharomyces cerevisiae* strain with efficient saccharification function obtained by the present invention was deposited on Dec. 23, 2014, at the China Center for Type Culture Collection, located in Wuhan University (Hongshan Qu Ba Yi Avenue, Wuhan, Hubei, 430072, China) and assigned a deposit Accession No. CCTCC M 2014657. This *Saccharomyces cerevisiae* strain will be released to the public irrevocably and without restriction/condition upon granting a US patent on this application, and will be maintained in the China Center for Type Culture Collection for a period of at least 30 years from the date of the deposit for the enforceable life of the patent or for a period of 5 years after the date of the most recent request of the deposit.

Expression Vector

The expression vector of the present invention comprises a nucleotide sequence encoding a glucoamylase, the nucleotide sequence is selected from a group consisting of:

(a) the amino acid sequence shown in SEQ ID NO: 16 is encoded by the nucleotide sequence;

(b) the sequence of glucoamylase-coding region of the nucleotide sequence has ≥80% identity with the nucleotide sequence shown in SEQ ID NO:15.

In another preferred embodiment, the sequence of the glucoamylase-coding region of the nucleotide sequence has ≥85% identity (preferably, ≥90% identity, more preferably, ≥95% identity, more preferably, ≥98% identity, even ≥99% identity) with the nucleotide sequence shown in SEQ ID NO:15.

In another preferred embodiment, the nucleotide sequence is shown in SEQ ID NO: 15.

In another preferred embodiment, the structure of the expression vector is:

ENO1p-GA-ENO1t-PDC1t-GA-ADH1p-delta5'-pUCori-CEN6/ARS-delta3'-loxP-TEF1p-KanMX-TEF1t-loxP Wherein GA is the polynucleotide according to claim 1; ENO1p, ADH1p, TEF1p are promoters; ENO1t, PDC1t, TEF1t are terminators; KanMX is a kanamycin/G418 resistance gene fragment; delta5', delta3' are delta fragments; pUCori-CEN6/ARS is a replicon sequence.

Yeast Host Cells

The yeast host cell of the present invention contains the above mentioned expression vector or has the sequence of glucoamylase-coding region of the above mentioned nucleotide sequence integrated into the genome thereof.

In another preferred embodiment, a fragment of the above mentioned expression vector obtained through NotI-linearization is integrated into the yeast host cell.

In the present invention, the yeast host cell does not contain an antibiotic resistance gene.

In the present invention, the yeast host cell is *Saccharomyces cerevisiae* with Accession No. CCTCC M 2014657.

The method for preparing the yeast host cell of the present invention comprises steps of:

(a) preparing three fragments, each of which is ENO1p-GA-ENO1t, delta5'-pUCori-CEN6/ARS-delta3'-loxP-TEF1p-KanMX-TEF1t-loxP, ADH1p-GA-PDC1t;

(b) connecting the three fragments obtained in step a) to obtain a target plasmid pYIE2-2GA-delta;

(c) linearizing pYIE2-2GA-delta obtained in step b) by NotI, transforming *Saccharomyces cerevisiae* to obtain a transformant;

(d) eliminating the resistance gene in the strain cultured from the transformant obtained in step c) to obtain the recombinant yeast.

In another preferred embodiment, the Accession No. of *Saccharomyces cerevisiae* used in step c) is CCTCC M94055.

In another preferred embodiment, delta5'-pUCori-CEN6/ARS-delta3'-loxP-TEF1p-KanMX-TEF1t-loxP is prepared by the following method:

(i) Using Primer 1 and Primer 2 as a primer pair, and using a pYIE2-XKS1-PPP-delta as a template to amplify a plasmid backbone fragment, wherein the structure of the plasmid backbone fragment is:

delta5'-pUCori-CEN6/ARS-delta3'-loxP-TEF1p-KanMX-TEF1t-loxP;

(ii) double-digesting the amplified plasmid backbone fragment by BamHI and KpnI to obtain a delta5'-pUCori-CEN6/ARS-delta3'-loxP-TEF1p-KanMX-TEF1t-loxP with a cohesive end.

In another preferred embodiment, ENO1p-GA-ENO1t is prepared by the following method:

(i) Using Primer 3 and Primer 4 as a primer pair, and using a genome of BY4741 as a template to amplify ENO1p; using Primer 5 and Primer 6 as a primer pair, and using the synthesized GA encoding sequence as a template to amplify GA; using Primer 7 and Primer 8 as a primer pair, and using a genome DNA of BY4741 as a template to amplify ENO1t;

(ii) mixing and using the three fragments obtained in step i) as a template, using Primer 3 and Primer 8 as a primer pair to amplify ENO1p-GA-ENO1t fragment by overlap PCR;

(iii) double-digesting the fragment amplified and obtained in step ii) by KpnI and NdeI to obtain an ENO1p-GA-ENO1t fragment with a cohesive end.

In another preferred embodiment, the ADH1p-GA-PDC1t fragment is prepared by the following method:

(i) Using Primer 9 and Primer 10 as a primer pair, and using genome of BY4741 as a template to amplify ADH1p; using Primer 11 and Primer 12 as a primer pair, and using a synthesized GA encoding sequence as a template to amplify GA; using Primer 13 and Primer 14 as a primer pair, and using a genome of BY4741 as a template to amplify PDC1t;

(ii) mixing and using the three fragments obtained in step i) as a template, using Primer 9 and Primer 14 as a primer pair to amplify an ADH1p-GA-PDC1t fragment by overlap PCR;

(iii) double-digesting the fragment amplified and obtained in step ii) by NdeI and BamHI to obtain an ADH1p-GA-PDC1t fragment with a cohesive end.

In another preferred embodiment, the resistance gene in the strain cultured from the transformant obtained in step c) is eliminated by the following method:

(i) transferring pSH47-hph1 into the strain cultured from the transformant, using galactose to induce the expression of Cre enzyme to eliminate G418 resistance;

(ii) eliminating the pSH47-hph plasmid by subculture.

Application

The yeast host cells of the present invention can be used to produce glucoamylases or for producing ethanol through fermentation.

In another preferred embodiment, the fermentation is a fermentation using one or more of corn, sugarcane, wheat, and cassava as a raw material.

The method for producing glucoamylase provided by the present invention comprises following steps:

(a) under suitable expression conditions, culturing the yeast host cell of the present invention, thereby expressing glucoamylase;

(b) isolating and purifying the glucoamylase expressed in step (a).

In the method for producing ethanol provided by the present invention, the yeast host cell of the present invention is used for producing ethanol through fermentation.

The features mentioned above, or the features mentioned in the embodiments, may be combined in any combination. All features disclosed in this specification may be used in conjunction with any form of the composition, and each of the features disclosed in the specification may be substituted by any alternative feature that provides the same, equal or similar purpose. Thus, unless otherwise specified, the features disclosed are only general examples of equal or similar features.

The advantages of the present invention are as follows:

(1) The present invention constructs a novel recombinant yeast.

(2) The recombinant yeast of the present invention has an efficient saccharification function and is used for fermentation to produce ethanol, which can effectively reduce the production cost of ethanol.

(3) The yeast cells obtained from fermentation can be used as feed additives for livestock and poultry and other animals. The saccharifying enzyme present in them can help to promote the digestion of animals.

The invention will be further illustrated with reference to the following specific examples. It is to be understood that these examples are only intended to illustrate the invention, but not to limit the scope of the invention. For the experimental methods in the following examples without particular conditions, they are performed under routine conditions (eg. Sambrook et al., Molecular Cloning: A Laboratory Manual (New York: Cold Spring Harbor Laboratory Press, 1989) or as instructed by the manufacturer. Unless otherwise specified, all percentages, ratios, proportions or parts are by weight.

Unless otherwise defined, all professional and scientific terms used herein are of the same meaning as those skilled in the art are familiar with. In addition, any method and material similar to or equivalent to the contents described may be applied to the method of the present invention. The preferred embodiments and materials described herein are for exemplary purposes only.

General Method

The corresponding experiments of the following examples are performed with reference to the following documents and apparatus in the present invention.

1. Molecular biology operations such as *E. coli* culture, competent cell preparation and transformation, plasmid extraction, restriction endonuclease digestion, PCR and the like are described in the "Molecular Cloning Experiment Guide" (Sambrook et al., 2nd ed., 1996).

2. Yeast culture, transformation and other operations are described in the "Experimental guide to the method of yeast genetics" (Adam et al., 2000).

3. Detection for the ethanol content is referring to the use of gas chromatography (Determination of Ethanol in Xylose Fermentation Broth by Gas Chromatography, wine, 1" ed., 2005).

4. Glucose analyzer is used for the detection of the Glucose content (Shandong Academy of Sciences).

EXAMPLE 1

Construction of the Target Plasmid pYIE2-2GA-Delta

The whole gene was synthesized according to a coding sequence of a saccharifying enzyme sequence from *Saccharomycopsis fibuligera* (AJ311587, available at http://www.ncbi.nlm.nih.gov/nuccore/19032256), wherein the coding sequence of a saccharifying enzyme sequence is optimized according to a codon of a *Saccharomyces cerevisiae*. (Hereinafter abbreviated as GA)

1) Primer 1 (SEQ ID NO: 1) and Primer 2 (SEQ ID NO: 2) were used as a primer pair and pYIE2-XKS1-PPP-delta was used as a template to perform conventional PCR amplification for obtaining the amplified product. The amplified product was digested with BamHI and KpnI to give the fragment 1.

2) Primer 3 (SEQ ID NO: 3) and Primer 4 (SEQ ID NO: 4) were used as a primer pair for PCR amplification with genome of BY4741 (commercially available from the EUROpean *Saccharomyces Cerevisiae* ARchive for Functional analysis) as a template to obtain a amplified product, recorded as an amplification product ENO1p; Primer 5 (SEQ ID NO: 5) and Primer 6 (SEQ ID NO: 6) were used as a primer pair to amplify GA with a synthesized GA coding sequence (SEQ ID NO: 15) as a template; Primer 7 (SEQ ID NO: 7) and Primer 8 (SEQ ID NO: 8) were used as a primer pair to amplify ENO1t with a genomic DNA of BY4741 as a template.

Three of the above amplification products were mixed and used as templates, and Primer 3 and Primer 8 were used as a primer pair for overlap PCR to amplify ENO1p-GA-ENO1t fragment, which was digested by tKpnI and NdeI for use, to give fragment 2.

3) Primer 9 (SEQ ID NO: 19) and Primer 10 (SEQ ID NO: 10) were used as a primer pair to amplify ADH1p with a genome of BY4741 as a template; Primer 11 (SEQ ID NO: 11) and Primer 12 (SEQ ID NO: 12) were used as a primer pair to amplify GA with a synthesized GA coding sequence as a template; Primer 13 (SEQ ID NO: 13) and Primer 14 (SEQ ID NO: 14) were used as a primer pair to amplify PDC1t with a genome of BY4741 as a template.

3 fragments were mixed and used as templates, and Primer 9 and Primer 14 were used as a primer pair for overlap PCR to amplify ADH1p-GA-PDC1t fragment, which was digested by NdeI and BamHI for use, to give fragment 3.

4) The three fragments obtained in the above three steps (fragment 1, fragment 2, fragment 3) were ligated to obtain target plasmid of pYIE2-2GA-delta, the structure of which is shown in FIG. 1. Two copies of GA fragment in the plasmid were used for the expression of saccharifying enzyme, and a delta fragment in the plasmid was used for integration into GA sites of Saccharomyces cerevisiae.

In this plasmid, the constructs containing the exogenous GA sites are as follows:

ENO1p-GA-ENO1t-PDC1t-GA-ADH1p-delta5'-pUCori-CEN6/ARS-delta3'-loxP-TEF1p-KanMX-TEF1t-loxP Wherein GA is the polynucleotide according to claim 1; ENO1p, ADH1p, TEF1p are the promoters; ENO1t, PDC1t, TEF1t are the terminators; KanMX is a kanamycin/G418 resistance gene fragment; delta5', delta3' are delta fragments; pUCori-CEN6/ARS is a replicon sequence.

The plasmid of pYIE2-XKS1-PPP-delta used in this example was constructed as follows:

1. Homologous arm sequences at the integration site were amplified and integrated by PCR;

Genome of BY4742 was used as a template and primer pairs of 1/2, 7/8 were respectively used for PCR amplification to obtain the upstream and downstream homologous arm sequences.

2. Replicon sequences of E. coli and Saccharomyces cerevisiae were amplified by PCR:

pSH47 (commercially available from EUROSCARF, EUROpean Saccharomyces Cerevisiae ARchive for Functional Analysis) was used as a template, and primer pairs 3/4, 5/6 were respectively used for PCR amplification to obtain Ecori and Scori sequences.

3. delta-up-EcoriScori-delta-dn fragment was obtained by OE-PCR amplification.

4. loxP-G418-loxP fragment was obtained by PCR amplification pUG6 (commercially available from EUROSCARF) was used as a template, and primer pair 9/10 was used for the amplification to obtain G418 resistant expression cassette with a loxP at both ends.

5. ADH1p-XKS1-XKS1t fragment was obtained by PCR amplification

Genome DNA of CIBTS0573 (see BMC Biotechnology 2013, 13: 110) was used as a template, and primer pair 11/12 was used for the amplification to obtain XKSJ expression cassette.

6. TPI1p-TAL1-TAL1t fragment was obtained by PCR amplification

Genome DNA of CIBTS0573 was used as a template, and primer pair 13/14 was used for the amplification to obtain TAL1 expression cassette.

7. PGK1p-RPE1-RPE1t fragment was obtained by PCR amplification Genome DNA of CIBTS0573 was used as a template, and primer pair 15/16 was used for the amplification to obtain RPE1 expression cassette.

8. FBA1p-TKL1-TKL1t fragment was obtained by PCR amplification Genome DNA of CIBTS0573 was used as a template, and primer pair 17/18 was used for the amplification to obtain TKL1 expression cassette.

9. PDC1p-RKI1-RKI1t fragment was obtained by PCR amplification CIBTS0573 was used as a template, and primer pair 19/20 was used for the amplification to obtain RKI1 expression cassette.

10. 7 fragments obtained in 3-9 were in vivo assembled to give plasmid pYIE2-Xks1-PPP-delta.

The sequences of the above primer pairs 1/2, 3/4, 5/6, 7/8, 9/10, 11/12, 13/14, 15/16 and 17/18 are shown in Table 1.

The above seven fragments were mixed and transformed into BY4741, and the method described in Methods Enzymol. 2012; 517: 203-24 was used for combination to obtain the correct pYIE2-Xks1-PPP-delta plasmid. It is noteworthy that the expression box fragments of XKS1, TAL1 and other genes in the plasmid will not enter the subsequent steps, and only the vector backbone sequence of delta5'-pUCori-CEN6/ARS-delta3'-loxP-TEF1p-KanMX-TEF1t-loxP will enter into the subsequent test steps.

TABLE 1 primer sequence

| NO. | SEQ ID NO. | name | sequence |
|---|---|---|---|
| 1 | 17 | dvdelta-up-f | ttcaaatcttgtttgtttgcccataccagcagtactgttggaatagaaatcaactatc |
| 2 | 18 | dvdelta-up-r | aaaccgcctctgcggccgcctaatattacgattattcctc |
| 3 | 19 | dvecscori (delta)-f | aatattaggcggccgcagaggcggtttgcgtattgggcgc |
| 4 | 20 | pucori-r | aaatatgtatccgctcatgagatctaggtgaagatccttttttgat |
| 5 | 21 | cen/ars-f | aaaggatcttcacctagatctcatgagcggatacatatttgaatg |

TABLE 1-continued primer sequence

| NO. | SEQ ID NO. | name | sequence |
|---|---|---|---|
| 6 | 22 | dvecscori (delta)-r | tctacatagcggccgcagccccgacacccgccaacacccg |
| 7 | 23 | dvdelta-dn-f | gtgtcggggctgcggccgctatgtagaaatatagattcca |
| 8 | 24 | dvdelta-dn-r | gttgtcgacctgcagcgtacgaagcttcagctggcatgggggttctctggaacagctga |
| 9 | 25 | dvg418(delta)-f | cacctgcttcatcagctgttccagagaaccccatgccagctgaagcttcgtacgctgca |
| 10 | 26 | dvg418r | ctcatcgtgatgtagtcaaccctatcttgattaggccactagtggatctgatatcacc |
| 11 | 27 | dvadh1pf | gaagttattaggtgatatcagatccactagtggcctaaaacaagaagagggttgactaca |
| 12 | 28 | xks1-r | tcaaaaaaatggcattattctaagtaagttaaatatccgtaatctttaaacactaaaagcgctaatttgatttgtctctc |
| 13 | 29 | tpi1p-f | tatgaaagggtgagcgaccagcaacgagagagacaaatcaaattagcgcttttagtgtttaaagattacggatatttaac |
| 14 | 30 | tal1-r | ctcacgagtaattcttgcaaatgcctattatgcagatgttataatatctgtgcgtttgattcaggtcaaaatggattcag |
| 15 | 31 | pgk1p-f | cacaatgatgttttcgatgctgtaaacgtccctgaatccattttgacctgaatcaaacgcacagatattataacatctgc |
| 16 | 32 | rpe1-r | atttacagaagttggaaggctggtattgttgttcaagccagcggtgccagttggaaggacactttccaaaaagagagcta |
| 17 | 33 | fba1p-f | tagcatattttaagtttctctcgatttcttagctctcttttggaaagtgtccttccaactggcaccgctggcttgaac |
| 18 | 34 | tkl1-r | gcttgtttatcttgcacatcacatcagcggaacatatgctcaccagtcgcatgacttgaatggtgtgattctctcgaag |
| 19 | 35 | pdc1p-f | agcacatggccgagcttgaatgttaaaccccttcgagagaatcacaccattcaagtcatgcgactgggtgagcatatgttc |
| 20 | 36 | dvrki(delta)-r | tagttagtagatgatagttgatttctattccaacagtactgctggtatgggcaaacaaac |

EXAMPLE 2

Construction of Recombinant Yeast Strains

After PYIE2-2GA-delt was linearized by NotI, the target fragments were recovered. Yeast CCTCC M94055 was recombinantly transformed with the recovered fragments by conventional transformation method to obtain the yeast strain transformants with pYIE2-2GA-delt. The transformed colonies were verified by PCR and sequencing.

PSH47-hph was transformed into strains cultured from the above-mentioned transformant (*BMC Biotechnology* 2013, 13: 110), the expression of Cre enzyme was induced by galactose, and G418 resistance was eliminated, and then the pSH47-hph plasmid was eliminated through subculture, and finally the strains without resistance were obtained, which were deposited in China Center for Type Culture Collection (Wuchang Luojia Hill, Wuhan) with Accession No. CCTCC M 2014657.

EXAMPLE 3

Test Tubes Fermentation for Each Strain

The Tapioca chips were pulverized and sieved at 60 mesh, which was weighed according to 20 g/l of the medium and used as a carbon source for the ethanol fermentation. Meantime, YP (yeast extract 10 g/l, peptone 20 g/l) was added as a nitrogen source in the medium. Unless otherwise defined, the specific experimental operation refers to: Research on fermentation production of ethanol with the corn as a raw material, food and fermentation industry, 2nd ed., 2008.

Experimental Medium:

The first group: crushed Tapioca chips samples, sterilized, YP added

The second group: crushed Tapioca chips samples, weighed according to 20 g/l medium, amylase-treated, sterilized, YP added.

The third group: crushed Tapioca chips samples, weighed according to 20 g/l medium, amylase-treated, saccharifying enzyme-treated, sterilized, YP added.

Experimental Steps:

(1) Colonies on the plate were inoculated in YPD20 tube for 24 h, 30° C., 220 rpm.

(2) the strain liquid in the test tube was diluted for 20 times, OD600 was measured, inoculated into the above 3 kinds of media for anaerobic culture according to an inoculating dose of 0.5 g/l, liquid volume of 5 ml in a test tube, 30° C., and 250 rpm.

(3) cultured for 28h, sampled for the determination of the ethanol concentration and glucose.

The experimental results are shown in Table 2.

TABLE 2

Anaerobic test tube fermentation data for each strain in the Tapioca chips samples

| strain | medium | glucose (g/l) 0 h | glucose (g/l) 28 h | ethanol (g/l) 28 h |
|---|---|---|---|---|
| Control original strain | the first group | 0.00 | 0.00 | 0.00 |
| CCTCC M 2014657 | | 0.00 | 0.52 | 4.27 |
| Control original strain | the second group | 1.26 | 0.00 | 2.35 |
| CCTCC M 2014657 | | 1.26 | 0.10 | 6.35 |
| Control original strain | the third group | 17.70 | 0.00 | 6.64 |
| CCTCC M 2014657 | | 17.70 | 0.00 | 7.42 |

The results are shown as follows:

1 In the experiment of pulverized Tapioca chips sample, compared with the original strain, ethanol production of the strain obtained by the present invention is achieved.

2 In the experiment of amylase-treated sample, compared with the original strain, the yield of the strain obtained by the present invention is greatly improved.

3 In the experiment of sample treated with amylase+saccharifying enzyme, compared with the original strain, the yield of the strain obtained by the present invention was greatly improved.

EXAMPLE 4

Fermentation in a Fermentor for the Strain

Corn flour was used as a raw material for ethanol fermentation referring to the application of *Angel super-brewed dry yeast in the fermentation of alcohol and fermented rice*, Wine Science and Technology, 1$^{st}$ ed., 2005. Experiments with or without saccharifying enzyme added before the fermentation were performed.

TABLE 3

| | Ethanol yield for each strain | |
|---|---|---|
| | ethanol yield (without saccharifying enzyme, g/100 mL) | ethanol yield (with saccharifying enzyme, g/100 mL) |
| Control original strain | 0.2~0.3 | 10.0 |
| CCTCC M 2014657 | 7.0~7.5 | 10.1~10.2 |

The results show that when the saccharifying enzyme is added, the yield of each strain is substantially the same. When the saccharifying enzyme is not added, the yield of the strain obtained by the present invention is greatly improved.

It has been reported that when yeast with saccharifying enzyme activity is used for producing ethanol through fermentation, the yield of ethanol is about 3%. Recently, Mascoma (US) has successfully developed saccharifying yeast by expressing heterologous glucoamylase in *Saccharomyces cerevisiae*. The yeast is used for the production of fuel ethanol, which can reduce about ⅓ of the amount of saccharifying enzymes and save the cost for ethanol producers. Mascoma in collaboration with Lallemand, has successfully marketed the saccharifying yeast with trade name of "TransFerm®". However, this saccharified yeast developed by Mascoma can only improve the ethanol production to at most 4%.

In addition, when fermentation is performed in a fermentor without saccharifying enzyme, compared with the recombinant yeast obtained in the present invention with optimized GA, the yield of the recombinant yeast obtained without optimized GA is only about ¼.

It can be seen that the recombinant yeast obtained in the present invention with optimized GA can greatly improve the yield of ethanol, when fermentation is performed without saccharifying enzyme.

Deposit of Microorganisms

The *Saccharomyces cerevisiae* with efficient saccharification function obtained by the present invention has been deposited on Dec. 23, 2014, at the China Center for Type Culture Collection, located in Wuhan University, with Accession No. CCTCC M 2014657.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:

1. A yeast host cell, comprising an exogenous nucleic acid having a nucleotide sequence encoding a glucoamylase, wherein the nucleotide sequence is selected from the group consisting of:

(a) a nucleotide sequence encoding the amino acid sequence of SEQ ID NO: 16; and (b) a nucleotide sequence comprising SEQ ID NO:15 and encodes the glucoamylase, and wherein the yeast host cell is the Saccharomyces cerevisiae strain deposited with the China Center for Type Culture Collection as Deposit Accession No. CCTCC M 2014657.

2. A method for producing glucoamylase, comprising steps of:

(a) under a suitable expression condition, culturing the yeast host cell according to claim 1, thereby expressing the glucoamylase; and (b) isolating and purifying the glucoamylase expressed in step (a).

3. A method for producing a yeast host cell, comprising steps of:

(a) preparing three fragments, which is ENO1p-GA-ENO1t, delta5'-pUCori-CEN6/ARS-delta3'-loxP-TEF1p-KanMX-TEF1t-loxP, ADH 1p-GA- PDC1t, respectively;

(b) connecting the three fragments obtained in step a) to obtain a target plasmid, pYIE2-2GA-delta as in FIG. 1;

(c) linearizing pYIE2-2GA-delta obtained in step b) by NotI, and transforming Saccharomyces cerevisiae to obtain a transformant;

(d) eliminating the resistance gene in a strain cultured from the transformant obtained in step c) to obtain the recombinant yeast.

4. A method for producing ethanol, comprising:

(a) conducting fermentation in a fermentation system, which comprises the yeast host cell according to claim 1, and a raw material comprising one or more of corn, sugarcane, wheat, and cassava, thereby producing ethanol; and (b) isolating the ethanol from the fermentation system.

5. The method of claim 4, wherein in step (a), the fermentation system contains no exogenous saccharifying enzyme.

* * * * *